(12) United States Patent
Hisata et al.

(10) Patent No.: US 12,295,764 B2
(45) Date of Patent: May 13, 2025

(54) CONTROLLER FOR IMAGING APPARATUS

(71) Applicant: Hologic, Inc., Marlborough, MA (US)

(72) Inventors: Suzuko Hisata, Marlborough, MA (US); Mallory Anne Berko, Marlborough, MA (US); Jonathan Paul Girgenti, New Milford, CT (US); Timothy Wells, Manchester, CT (US)

(73) Assignee: Hologic, Inc., Marlborough, MA (US)

( * ) Notice: Subject to any disclaimer, the term of this patent is extended or adjusted under 35 U.S.C. 154(b) by 102 days.

(21) Appl. No.: 18/195,991

(22) Filed: May 11, 2023

(65) Prior Publication Data

US 2023/0346327 A1 Nov. 2, 2023

Related U.S. Application Data

(63) Continuation of application No. 17/405,218, filed on Aug. 18, 2021, now Pat. No. 11,684,331, which is a
(Continued)

(51) Int. Cl.
| | |
|---|---|
| A61B 6/00 | (2024.01) |
| A61B 6/02 | (2006.01) |
| A61B 6/04 | (2006.01) |
| A61B 6/46 | (2024.01) |
| A61B 6/50 | (2024.01) |
| A61B 6/10 | (2006.01) |
| A61B 6/42 | (2024.01) |

(52) U.S. Cl.
CPC ............ *A61B 6/4435* (2013.01); *A61B 6/025* (2013.01); *A61B 6/0414* (2013.01); *A61B 6/462* (2013.01); *A61B 6/467* (2013.01); *A61B 6/502* (2013.01); *A61B 6/54* (2013.01); *A61B 6/107* (2013.01); *A61B 6/4291* (2013.01); *A61B 6/461* (2013.01)

(58) Field of Classification Search
CPC .... A61B 6/00; A61B 6/02; A61B 6/04; A61B 6/025; A61B 6/0414; A61B 6/4435; A61B 6/462; A61B 6/467; A61B 6/502; A61B 6/54; A61B 6/107; A61B 6/4291; A61B 6/461
See application file for complete search history.

(56) References Cited

U.S. PATENT DOCUMENTS 11,123,030 B2 9/2021 Hisata
11,684,331 B2 6/2023 Hisata
(Continued)

FOREIGN PATENT DOCUMENTS

CN 105982684 A 10/2016
EP 0775467 5/1997
(Continued)

OTHER PUBLICATIONS

European Extended Search Report in Application EP 17873420.8, dated Jun. 25, 2020, 6 pages.
(Continued)

*Primary Examiner* — Jurie Yun
(74) *Attorney, Agent, or Firm* — Merchant & Gould P.C.

(57) ABSTRACT

An apparatus has an upright gantry. A tube arm assembly and a compression arm assembly are rotatably coupled to the gantry. The tube arm assembly independently rotates relative to the compression arm assembly. A controller disposed on the gantry is operably connected to at least one of the tube arm assembly and the compression arm assembly.

20 Claims, 9 Drawing Sheets

Related U.S. Application Data continuation of application No. 16/463,570, filed as application No. PCT/US2017/063069 on Nov. 22, 2017, now Pat. No. 11,123,030.

(60) Provisional application No. 62/426,349, filed on Nov. 25, 2016.

(56) References Cited

U.S. PATENT DOCUMENTS

| | | |
|---|---|---|
| 2005/0129172 A1 | 6/2005 | Mertelmeier |
| 2009/0304159 A1 | 12/2009 | Meer et al. |
| 2011/0021947 A1 | 1/2011 | Nakayama et al. |
| 2013/0331682 A1 | 12/2013 | Ohta et al. |
| 2014/0126687 A1 | 5/2014 | Yoshikawa et al. |
| 2014/0328469 A1 | 11/2014 | Lee et al. |
| 2015/0049859 A1 | 2/2015 | DeFreitas et al. |
| 2017/0020471 A1 | 1/2017 | Laukkanen |

FOREIGN PATENT DOCUMENTS

| | | |
|---|---|---|
| EP | 2727534 | 5/2014 |
| JP | 2010-005157 A | 1/2010 |
| JP | 2010-110571 A | 5/2010 |
| JP | 2013-066784 A | 4/2013 |
| KR | 20160091382 | 8/2016 |
| KR | 1020160091958 | 8/2016 |
| WO | 2009/068732 | 6/2009 |
| WO | 2010/028208 | 3/2010 |

OTHER PUBLICATIONS

PCT International Search Report and Written Opinion of the International Searching Authority for International Patent Application No. PCT/US2017/063069 dated Feb. 9, 2018, 13 pages.

PCT International Preliminary Report on Patentability in Application PCT/US2017/063069, dated Jun. 6, 2019, 8 pages.

CONTROLLER FOR IMAGING APPARATUS

CROSS-REFERENCE TO RELATED APPLICATIONS

This application is a continuation of U.S. patent application Ser. No. 17/405,218, now U.S. Pat. No. 11,684,331, filed Aug. 18, 2021, which is a continuation of U.S. patent application Ser. No. 16/463,570, now U.S. Pat. No. 11,123,030, filed May 23, 2019, which application is a National Stage Application of PCT/US2017/063069, filed Nov. 22, 2017, which claims priority to U.S. Provisional Patent Application No. 62/426,349, filed Nov. 25, 2016, the disclosures of which are hereby incorporated by reference herein in their entireties. To the extent appropriate, a claim of priority is made to each of the above disclosed applications.

BACKGROUND

X-ray mammography has long been a screening modality for breast cancer and other lesions, and also has been relied on for diagnostic and other purposes. For mammograms, a cone-shaped or pyramid-shaped x-ray beam passes through the compressed breast and forms a two-dimensional projection image. Any one of a number of orientations can be used, such as cranial-caudal (CC) or mediolateral-oblique (MLO) orientation. Another imaging modality is breast x-ray tomosynthesis. The technology typically involves taking two-dimensional (2D) projection images of the immobilized breast at each of a number of angles of the x-ray beam relative to the breast and processing the resulting x-ray measurements to reconstruct images of breast slices that typically are in planes transverse to the x-ray beam axis, such as parallel to the image plane of a mammogram of the same breast.

SUMMARY

In one aspect, the technology relates to an apparatus having: an upright gantry; a tube arm assembly rotatably coupled to the upright gantry; a compression arm assembly rotatably coupled to the upright gantry, wherein the tube arm assembly is at least partially independently rotatable relative to the compression arm assembly; and a controller disposed on the upright gantry and operably connected to at least one of the tube arm assembly and the compression arm assembly. In an example, the controller includes a first controller disposed on a first side of the upright gantry and a second controller disposed on a second side of the upright gantry. In another example, the controller includes two controllers disposed on opposite sides of the gantry. In yet another example, the controller is at least partially flush with an outer housing of the gantry. In still another example, the controller includes a longitudinal axis substantially parallel to a longitudinal axis of the upright gantry.

In another example of the above aspect, a first side of the controller projects a first distance from an outer housing of the gantry and wherein a second side of the controller projects a second distance from the outer housing of the gantry, wherein the first distance is less than the second distance. In an example, the controller includes at least one of a button, a dial, a knob, and a graphic user interface. In another example, a front face of the controller is disposed at an angle to an outer housing of the gantry. In yet another example, the controller includes a substantially D-shaped outline. In still another example, the controller is disposed a distance above a floor surface greater than one-half a total height of the gantry.

In another example of the above aspect, the controller includes a locating feature. In an example, the locating feature includes at least one of a recess, a raised feature, and a button. In another example, the controller faces away from a patient station.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

Figure 1:
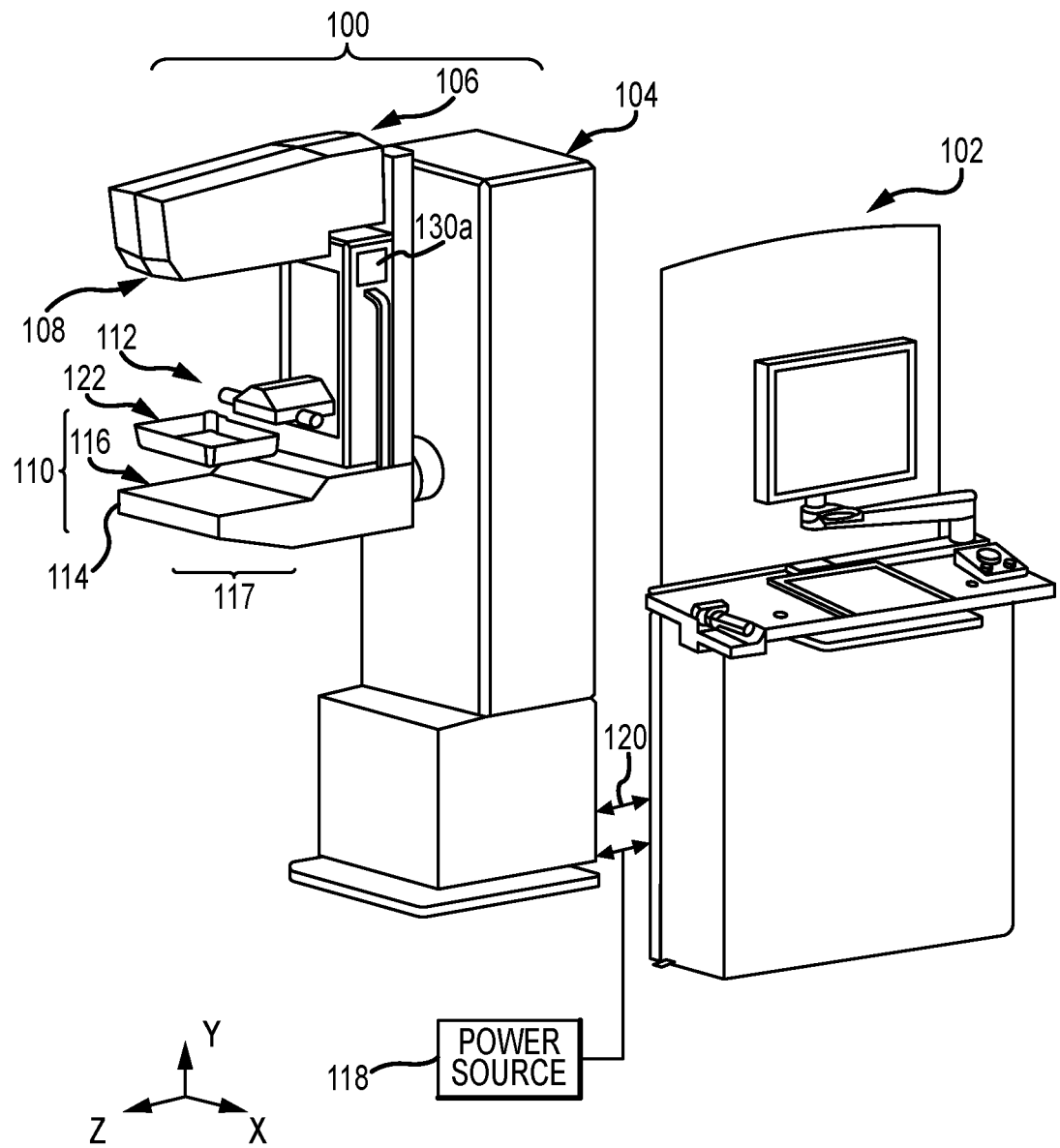
FIG. 1 is a perspective view of a gantry and an acquisition workstation in accordance with the prior art.
Figure 2:
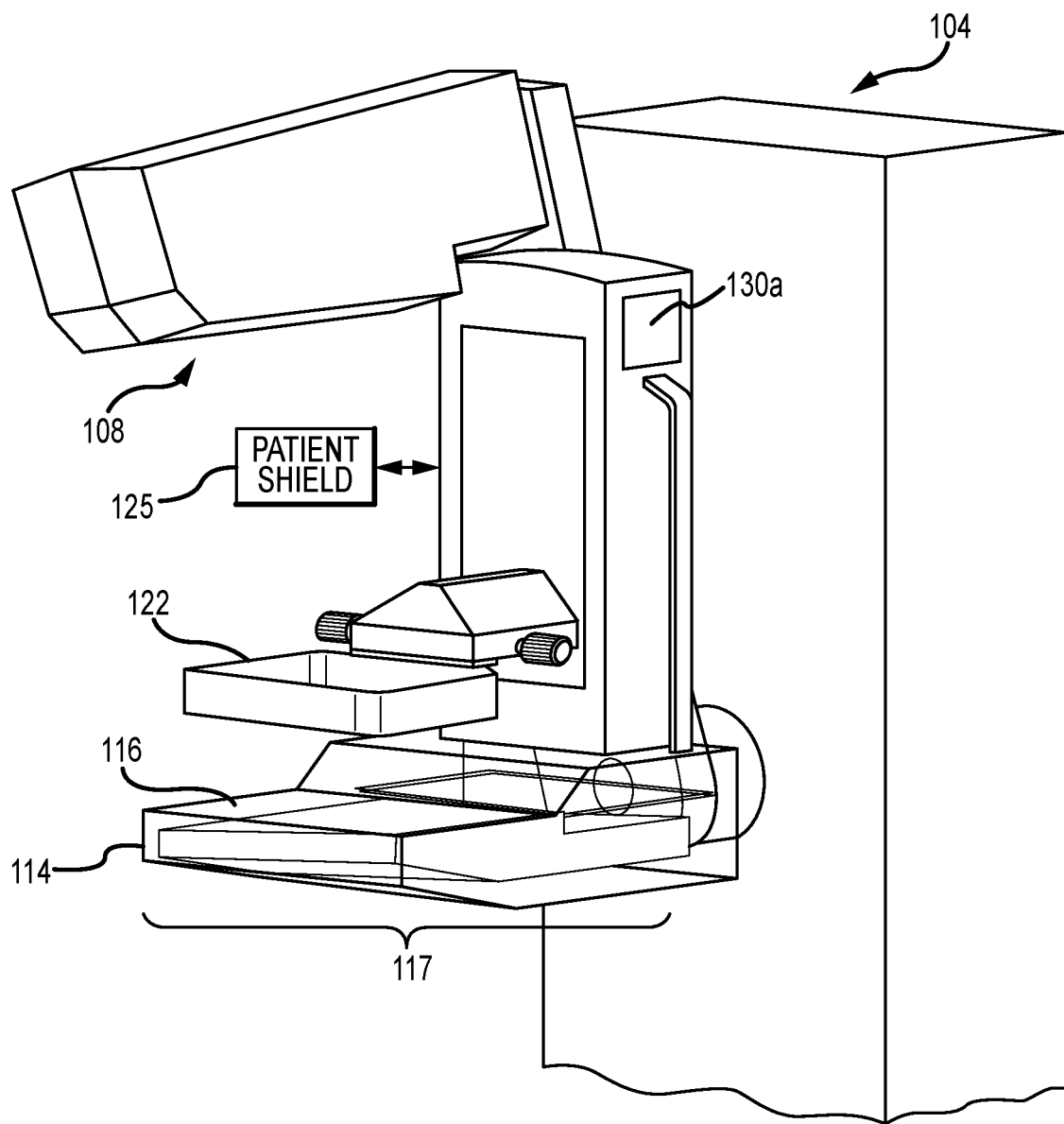
FIG. 2 is an enlarged view of a portion of the system of FIG. 1, with a tube arm assembly in a rotated position.

The present technology relates to a breast imaging systems that are used to generate mammograms and/or tomosynthesis images of the breast. In use, a technician places a breast of a patient on a platform of an imaging system and compresses the breast against the platform with a breast compression plate or paddle. One or more x-ray images are then taken of the breast and processed for analysis.

FIGS. 1-4 illustrate a non-limiting example of a multi-mode mammography/tomosynthesis system comprising a floor-mounted, upright gantry 100 and a data acquisition work-station 102. Gantry 100 includes a housing 104 supporting a tube arm assembly 106 rotatably mounted thereon to pivot about a horizontal axis 402 (FIG. 4) and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin filters, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis 402, is a compression arm assembly 110 that includes a compression device 112 having to a compression plate or paddle 122 and a receptor housing 114 having an upper surface 116 serving as a breast plate and enclosing a receptor subsystem system 117 comprising a flat panel x-ray receptor 119, a retractable anti-scatter grid 121, and a mechanism (not shown) for driving and retracting anti-scatter grid 121. Housing 104 also encloses the following components: a vertical travel assembly 404 for moving tube arm assembly 106 and compression arm assembly 110 up and down to accommodate a particular patient or imaging position, a tube arm assembly rotation mechanism 406 to rotate tube arm assembly 106 about axis 402 for different imaging positions, a receptor subsystem rotation mechanism 408 for rotating components of receptor subsystem 117 (such as x-ray receptor 119) about axis 402 to accommodate different operation modes, and couple/uncouple mechanism 410 to selectively couple or uncouple tube arm assembly 106 and compression arm assembly 110 to and from each other, and tube arm assembly 106 and receptor subsystem 117 to and from each other. Housing 104 also encloses suitable motors and electrical and mechanical components and connections to implement the functions discussed here. A patient shield 125, schematically illustrated in FIG. 2, can be secured to compression arm assembly 110 to provide a mechanical interlock against patient contact with the rotating x-ray tube arm assembly 106. A spacer 1002 (FIG. 4) may be used for different degrees of magnification.

Work-station 102 comprises components similar to those in the Selenia® Dimensions® mammography system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia® Dimensions® system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

The gantry 100 may also include one or more controllers 130 that may be used for certain functions of the gantry 100. The controller 130 is disposed on the compression arm assembly 110 and may be used by a technician to raise or lower the compression arm assembly 110 (e.g., for patients of different heights), raise or lower the compression device 112, rotate the tube arm assembly 106, or perform other functions. A controller 130a, 130b is located on either side of the compression arm assembly 110, so as to be more easily accessible by a technician. While locating the controller 130a, 130b on the compression arm assembly 110 may be convenient for the technician, rotation of the tube arm assembly 106 and/or compression arm assembly 110 may make access thereto difficult, as described below.

Figure 4:
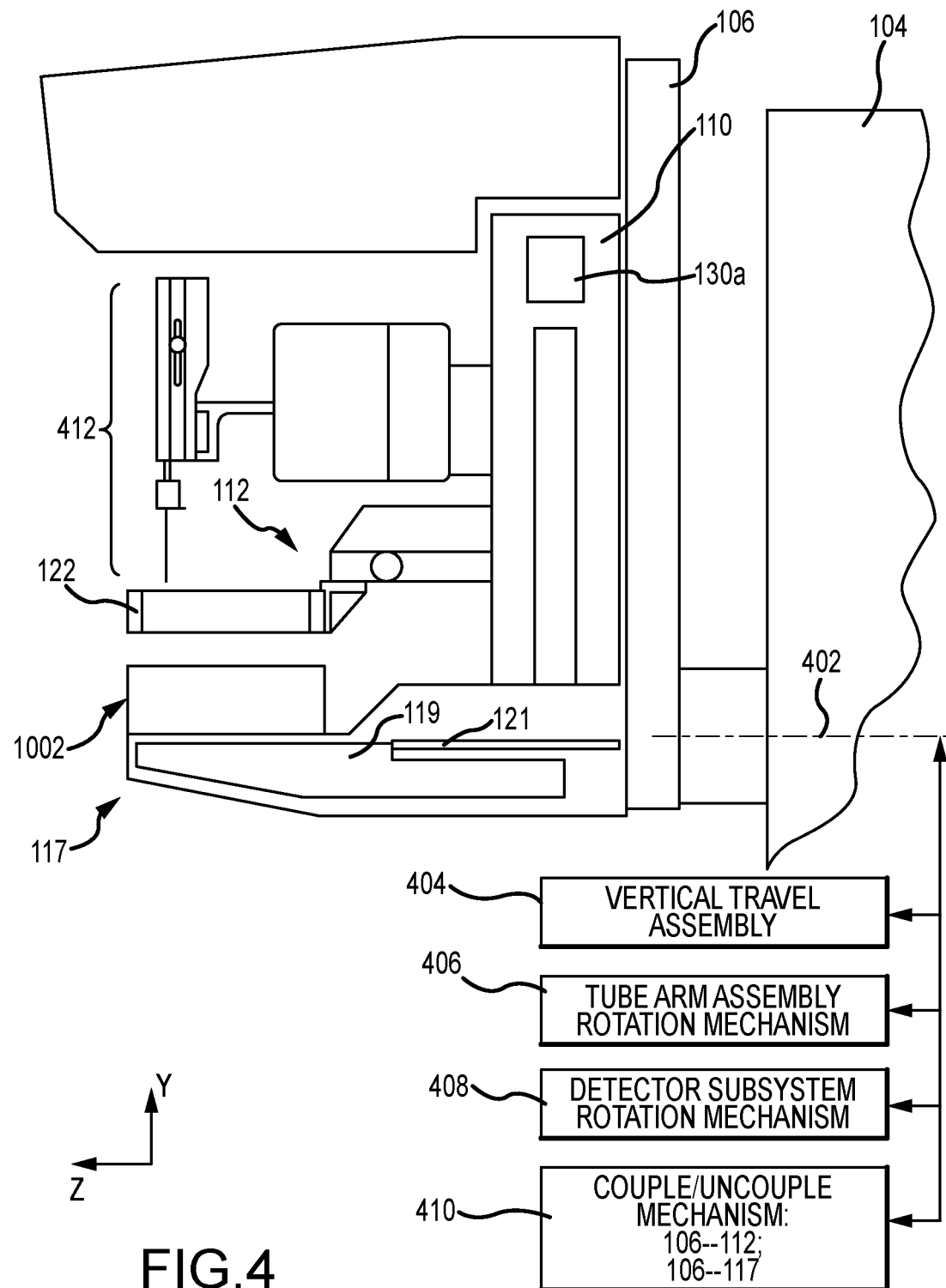
FIG. 4 is a side view of the apparatus of FIG. 2 with an optional biopsy station.

In standard mammography mode, typically used for screening mammography, tube arm assembly 106 and compression arm assembly 110 are coupled and locked together by 410 in a relative position such as seen in FIG. 1, such that an x-ray beam from x-ray tube assembly 108 illuminates x-ray receptor 119 when the patient's breast is compressed by compression device 112. In this mode, the system operates in a manner similar to said Selenia® Dimensions® system to take a mammogram. Vertical travel assembly 404 and tube arm rotation mechanism 406 can make vertical adjustments to accommodate a patient, and can rotate tube arm assembly 106 and compression arm assembly 110 together as a unit about axis 402 for different image orientations such as for CC and for MLO images. For example, tube arm assembly 106 and compression arm assembly 110 can rotate between −195° and +150° about axis 402. FIG. 4 depicts rotation of the tube arm assembly 106, which may limit access to the controller 130b. As in the Selenia® Dimensions® system, compression device 112 includes a compression paddle 122 that can move laterally, in a direction along the chest wall of a patient, to adjust for different imaging orientations. Typically, anti-scatter grid 121 is over x-ray receptor 119 in the standard mammography mode to reduce the effect of x-ray scatter.

Figure 3:
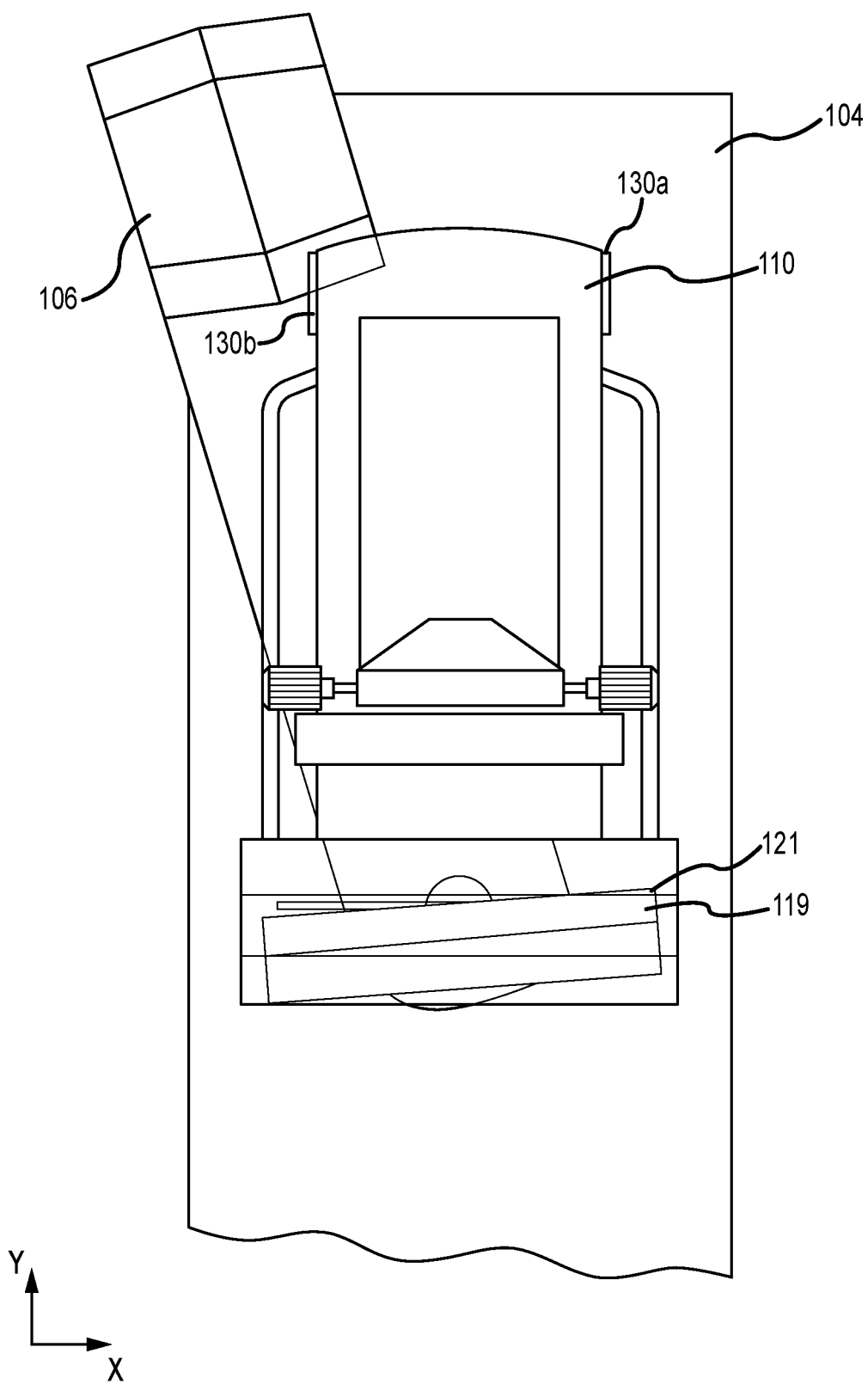
FIG. 3 is a front elevation of the apparatus of FIG. 2.

As noted above, both of the tube arm assembly 106 and the compression arm assembly 110 can rotate between −195° and +150° about axis 402. FIG. 3 depicts rotation of the tube arm assembly 106. In the depicted position, the rotated position of the tube arm assembly 106 may limit technician access to the controller 130b. Moreover, in circumstances where the compression arm assembly 110 is rotated, access may be further limited. For example, if the compression arm assembly 110 rotates counterclockwise from the position depicted in FIG. 3, the controller 130a will be extremely difficult to view, let alone activate, especially for technicians that are short of stature. As such, workflow may be impeded if either controller 130a, 130b becomes obstructed or otherwise difficult to reach.

Figure 5:
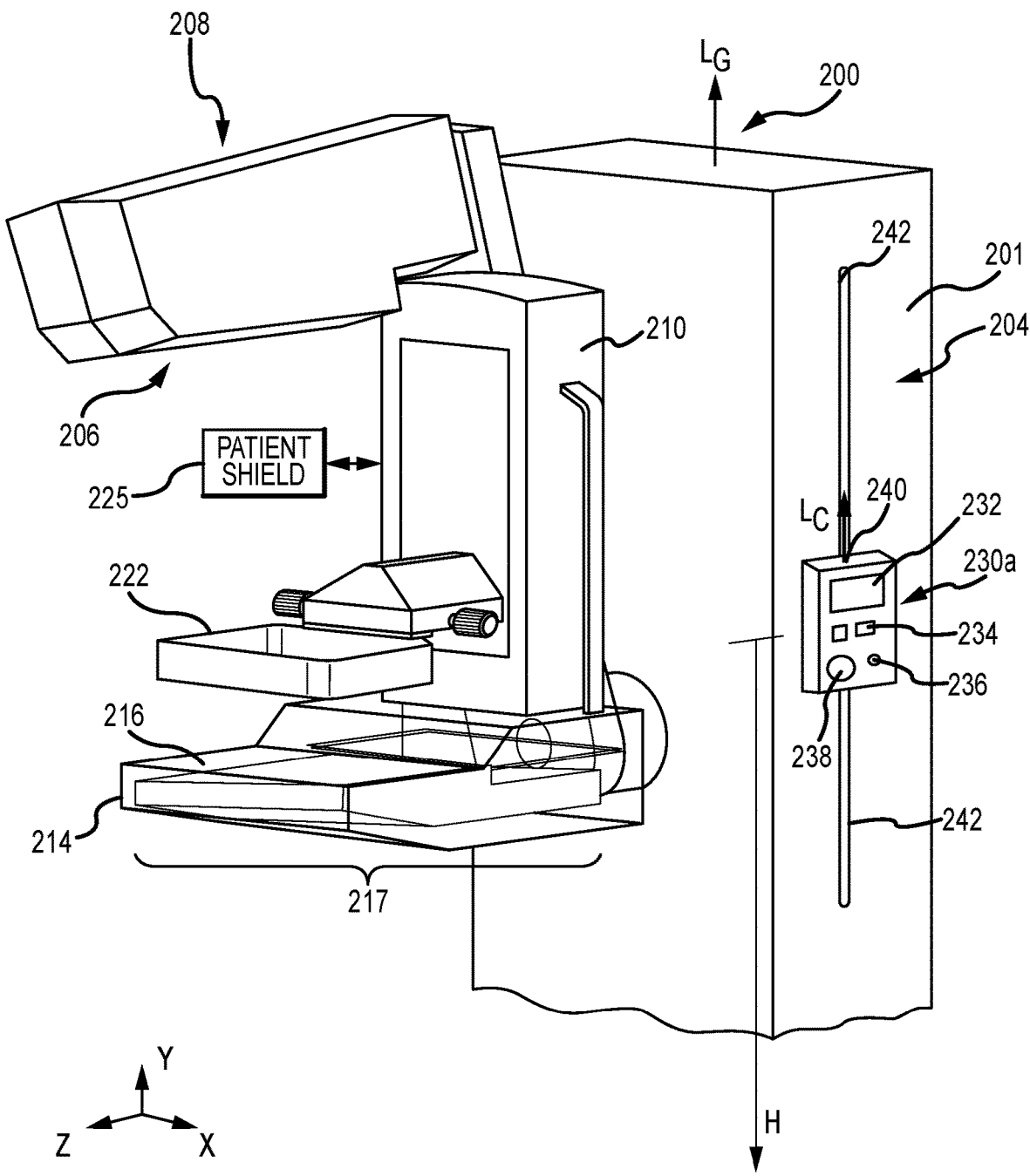
FIG. 5 is an enlarged view of an imaging apparatus, with a tube arm assembly in a rotated position.

FIG. 5 is an enlarged view of an imaging apparatus 200, with a tube arm assembly 206 in a rotated position. The imaging apparatus 200 may include any or all of the components depicted and described with regard to FIGS. 1-4. As such, not all of those components are necessarily depicted or described further in the following figures. A compression arm assembly 210 and patient shield 225 are also depicted. As in the previous figures, both the tube arm assembly 206 and compression arm assembly 210 may rotate relative to an upright housing 204 (in the form of a pillar having a rectangular, curved, or other shape) of a gantry 201. Rotation of the tube arm assembly 206 changes a position of the x-ray tube assembly 208 and an enclosed receptor subsystem system 217. Rotation of the compression arm assembly 210 changes a position of a receptor housing 214 and an upper surface 216 thereof, as well as a compression paddle 222. The imaging apparatus 200 of FIG. 5, however, incorporates a controller 230a on at least one side of the housing 204 of the upright gantry 201. A second controller may be disposed on an opposite side of the gantry 201, but is not visible in FIG. 5. The positioning of the controller 230a in such a location allows a technician to easily access the controller 230a, regardless of the position of the tube arm assembly 206, position of the compression arm assembly 210, height or reach of the technician, etc. For example, the controller 230a may be easily accessed whether the tube arm assembly 206 and compression arm assembly 210 are oriented for a CC or MLO orientation for an examination.

The controller 230a may include one or more components required to perform various actions or procedures. Such actions may include but are not limited to, rotation of the tube arm assembly 206, rotation or elevation change of the compression arm assembly 210, compression by the paddle 222 to the breast, and so on. Such components may include a graphic user (or touch-sensitive) interface 232, a button 234, a knob or dial 236, a fingerprint scanner 238 (to confirm authorized usage, e.g. or other type of biometric login), or other components. These components are supported in a controller housing 240 that may at least partially protrude from the housing 204 of the gantry 201. In the example of FIG. 5, the controller housing 240 is disposed proximate a slot 242 defined by the housing 204. The controller housing 240 may engage with a projection that extends from an interior of the gantry 201, through the slot 242, so as to be slidably moved along the slot 242. This may further increase the usability of the controller 230a, for technicians of different heights or reaches, for example. In other examples, however a vertical position of the controller 230a may be fixed relative to the gantry 201. In examples where the vertical position of the controller 230a is fixed, it may be desirable that the controller is disposed at a height H above a floor that is greater than one-half of the total height of the gantry 201, since technicians of different heights may be able to easily access a controller 230a so positioned.

Vertical sides of the controller housing 240 may be longer than top and bottom sides of the controller housing 240. As such, the controller housing 240 may define a longitudinal axis $L_C$ that is substantially parallel to a longitudinal axis $L_G$ of the gantry 201. Such a longer, narrower controller housing 240 may allow the controller to have a lower profile extending away from the gantry housing 204. This may prevent the controller 230a from being inadvertently bumped or contacted as a technician moves about the imaging apparatus 200. Other shapes are contemplated. For example, the controller 230a is depicted as having a rectangular outline. Controllers having circular, oval, D-shaped, or polygonal outlines are also contemplated. Such outlines may be utilized to match the aesthetics of the gantry 201.

Figure 6A:
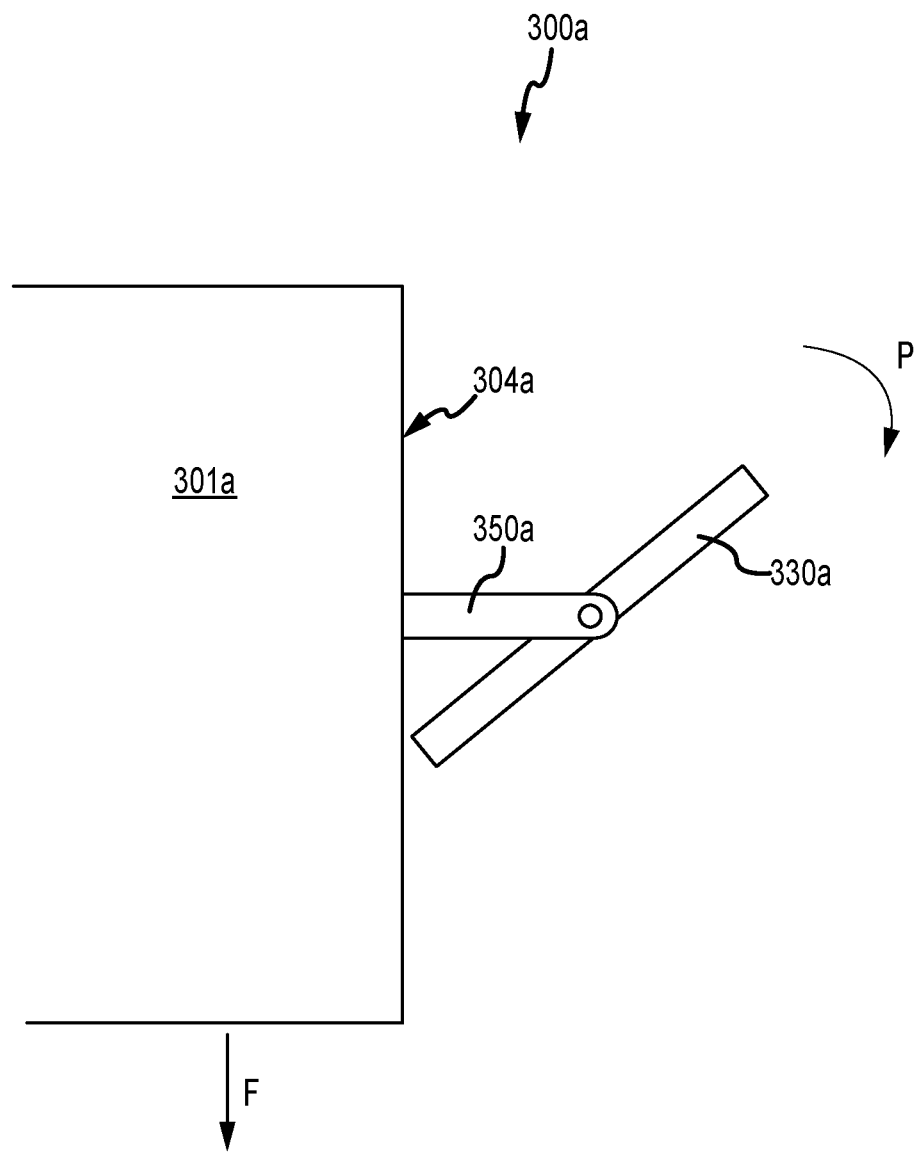
FIGS. 6A and 6B depict partial top views of a controller of an imaging apparatus.
Figure 6B:
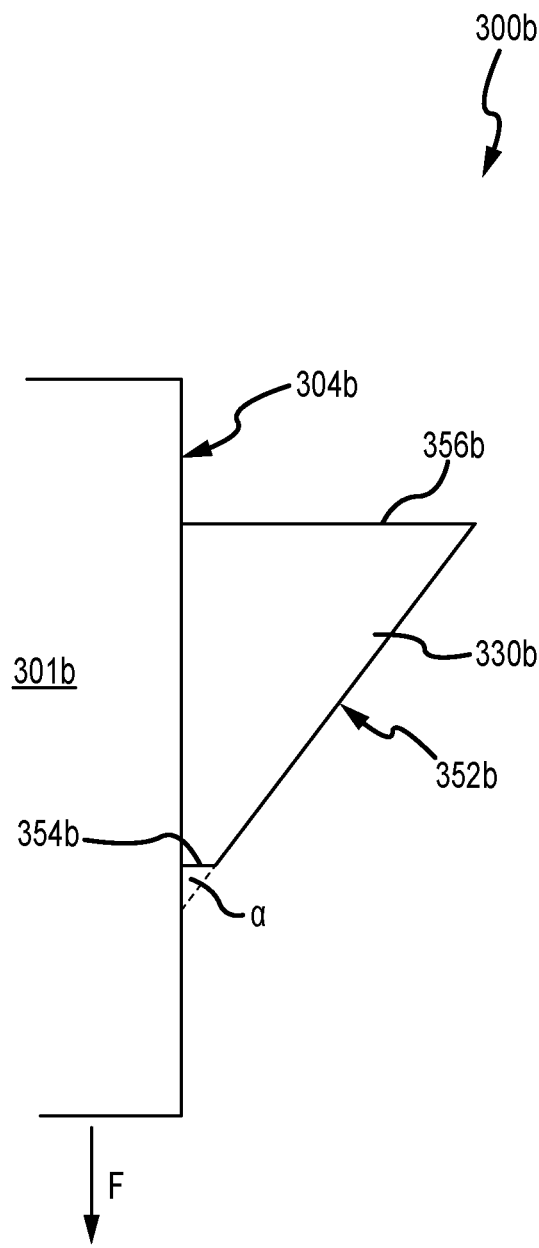

FIGS. 6A and 6B depict partial top views of a controller 330a, 330b of an imaging apparatus 300a, 300b. In FIG. 6A, the controller 330a is pivotable P about one or more brackets 350 that extend from a housing 304a of a gantry 301a. This allows the controller 330a to be more easily viewable by a technician working with a patient standing near the front F of the gantry 301a (e.g., a patient having a breast compressed for imaging).

In FIG. 6B, a front face 352b of a controller 330b is disposed at an angle α relative to a housing 304b of a gantry 301b. A first side 354b has a first length measured from the housing 304b, while a second side 356b has a second length measured therefrom. The second length is greater than the first length. By disposing the front face 352b at an angle, visibility of the front face 352b, which contains the control components, is increased. This is particularly useful for a technician working with a patient standing near a front face F of the gantry 301b. In certain examples, the first length of the first side 356b may be short enough such that the first side 356b is substantially flush with the housing 304b.

Figure 7:
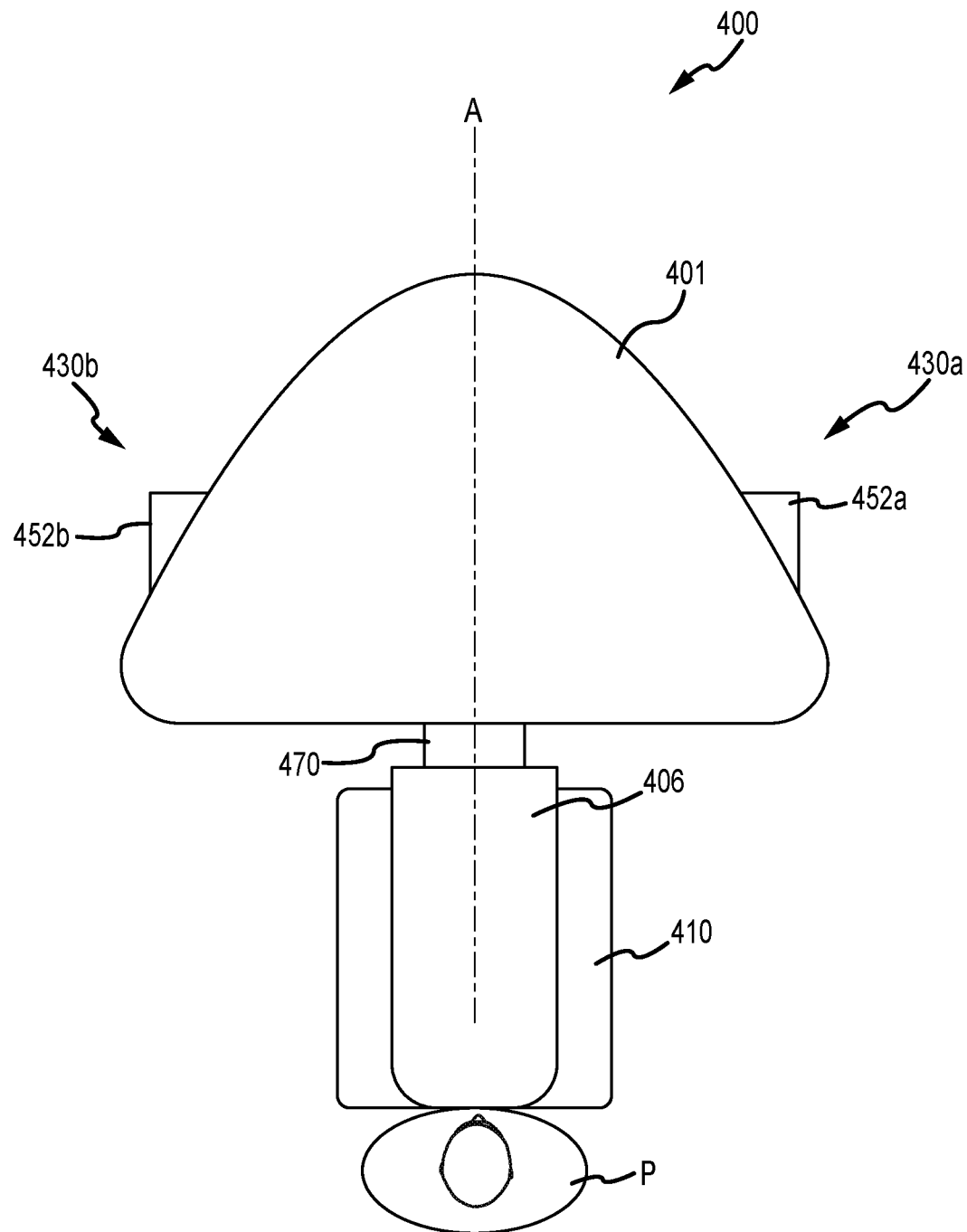
FIG. 7 depicts a top view of an imaging apparatus.

FIG. 7 depicts a top view of an imaging apparatus 400, including an upright gantry 401, a tube arm assembly 406, and a compression arm assembly 410. A patient P is located at a patient station (e.g., proximate the compression arm assembly 410 where a breast imaging procedure may be performed). An axis A extends through a collar 470 that extends from the gantry 401. Mechanisms within the collar 470 allow for rotation of both the tube arm assembly 406 and the compression arm assembly 410 about the axis A. Two controllers 430a, 430b are disposed on either side of the gantry 401. The front face 452a, 452b of each controller 430a, 430b face in a direction substantially away from the axis A. As such, the front faces 452a, 452b are generally out of view of the patient P. This may be advantageous, as flashings lights or other elements on the controllers 430a, 430b may cause the patient unnecessary anxiety if visible.

Figure 8:
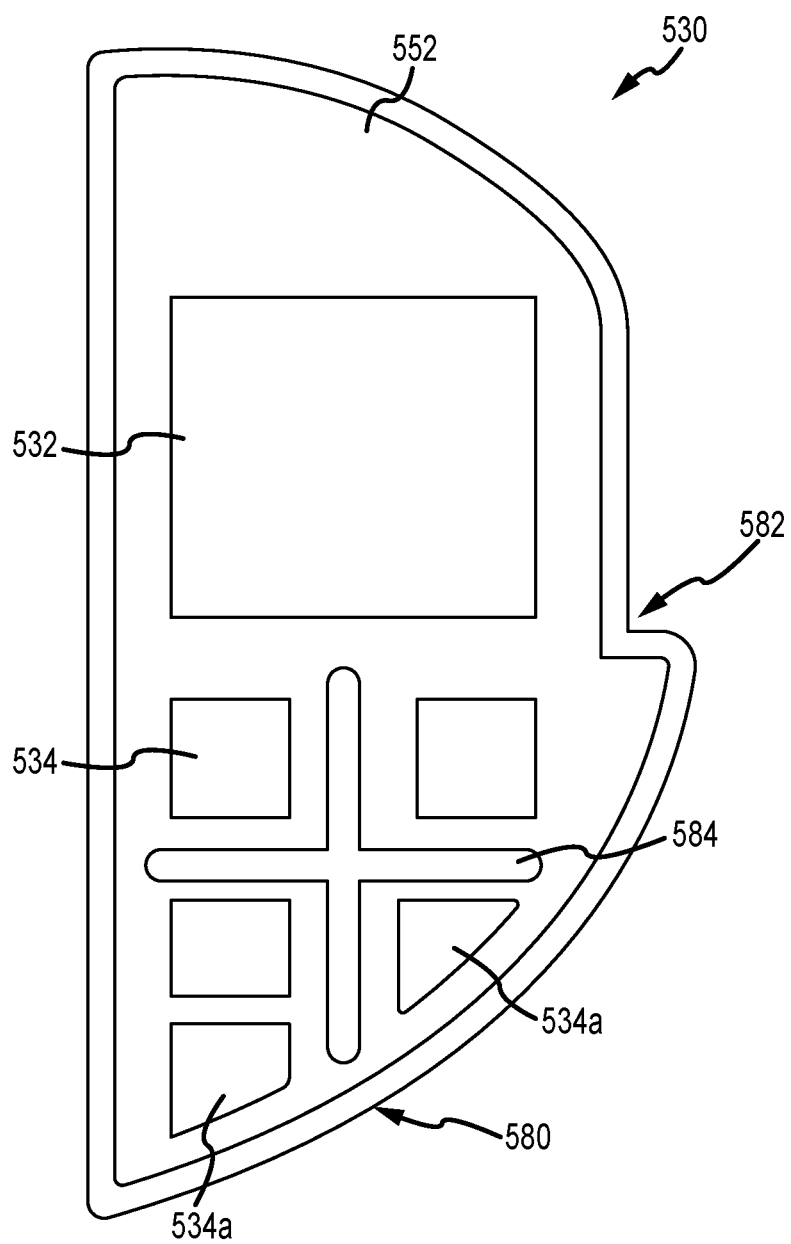
FIG. 8 depicts a front view of a controller.

FIG. 8 depicts a front view of a controller 530, specifically a substantially D-shaped controller. The front face 552 of the controller includes a display screen 532 which may act as a graphic user interface or a simple display. The front face 552 also includes a plurality of buttons 534. Certain buttons 534a may have an outer contour shaped to match an outer perimeter or contour 580 of the controller 530. The controller 530 also includes features that allow a technician to orient herself during use of the controller 530, without necessarily seeing the front face 552 and the components disposed thereon. Under such circumstances, the controller 530 may be used without being visible to the user. For example, the outer perimeter or contour 580 may define one or more recesses or cutouts 582 that, when touched, give an indication to a technician of the location of their hand relative to the front face 552. In the depicted example, contacting the recess 582 would indicate to the technician that her hand is disposed proximate the display screen 532. A raised feature 584, for example, disposed near or between buttons 534 may also be used to orient a technician to the controller 530 when the controller 530 is not visible. In another example, the controller 530 may include buttons 534 that are raised, lowered, or flush with the front face 552, to increase usability thereof.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. A multi-mode mammography/tomosynthesis system comprising:
   a floor-mounted, upright gantry having at least a patient facing front surface and an opposite rear surface, wherein the rear surface comprises a curved portion;
   a collar extending from the front surface and defining a rotation axis;
   a tube arm assembly rotatably coupled to the gantry at the collar;
   a compression arm assembly rotatably coupled to the gantry at the collar; and
   at least one controller configured to at least partially control one or more operations of the system, the at least one controller disposed on the gantry on the rear surface, wherein the at least one controller has a front face with a first side projecting a first distance from the rear surface and an opposing second side projecting a second distance from the rear surface, wherein the second distance is greater than the first distance, such that the front face is angled and at a fixed position relative to the rear surface of the gantry.

2. The multi-mode mammography/tomosynthesis system of claim 1, wherein the front face is out of view of a patient when the patient's breast is compressed in the compression arm assembly.

3. The multi-mode mammography/tomosynthesis system of claim 1, wherein the first distance is substantially flush with the rear surface of the gantry.

4. The multi-mode mammography/tomosynthesis system of claim 1, wherein the at least one controller comprises a first controller and a second controller, the first controller and the second controller symmetrically disposed on the rear surface on opposite sides of the rotation axis.

5. The multi-mode mammography/tomosynthesis system of claim 4, wherein the front face of the first controller is parallel to the front face of the second controller.

6. The multi-mode mammography/tomosynthesis system of claim 1, wherein the front face of the at least one controller faces a direction that is substantially away from the rotation axis.

7. The multi-mode mammography/tomosynthesis system of claim 1, wherein the at least one controller is disposed on the curved portion of the rear surface.

8. The multi-mode mammography/tomosynthesis system of claim 1, wherein the rear surface of the gantry that the at least one controller is disposed on includes one or more side surfaces.

9. The multi-mode mammography/tomosynthesis system of claim 1, wherein an outer perimeter of the front face of the at least one controller is contoured.

10. The multi-mode mammography/tomosynthesis system of claim 9, wherein the contoured outer perimeter of the front face defines one or more recesses or cutouts.

11. The multi-mode mammography/tomosynthesis system of claim 1, wherein the at least one controller has a D-shape.

12. The multi-mode mammography/tomosynthesis system of claim 1, further comprising a data acquisition work-station coupled in communication to the gantry, the data acquisition work-station having one or more image displays.

13. An apparatus comprising:
   an upright gantry having an outer housing and a substantially vertical gantry longitudinal axis;
   a tube arm assembly rotatably coupled to the upright gantry about a rotation axis;
   a compression arm assembly rotatably coupled to the upright gantry, wherein the tube arm assembly is at least partially independently rotatable around the rotation axis relative to the compression arm assembly; and
   a controller having a front face disposed at a fixed angle to the outer housing and operably connected to at least one of the tube arm assembly and the compression arm assembly, the front face faces away from a patient station, wherein the controller comprises a substantially vertical controller longitudinal axis substantially parallel to the gantry longitudinal axis, wherein the controller comprises a first side and a second side disposed parallel to the longitudinal axis, wherein the first side has a first length and the second side has a second length different than the first length.

14. The apparatus of claim 13, wherein the first side is disposed a first distance from the outer housing, and the second side is disposed a second distance from the outer housing, wherein the first distance is less than the second distance.

15. The apparatus of claim 14, wherein the first side is substantially flush with the outer housing of the gantry.

16. The apparatus of claim 15, wherein the second length is greater than the first length.

17. The apparatus of claim 13, wherein the controller comprises two controllers disposed on opposite sides of the gantry.

18. The apparatus of claim 13, wherein the controller comprises at least one of a button, a dial, a knob, and a touch screen.

19. The apparatus of claim 13, wherein an outer perimeter of the controller comprises a contour defining one or more recesses or cutouts.

20. The apparatus of claim 13, wherein the controller comprises a locating feature.

* * * * *